United States Patent
Majeti et al.

(10) Patent No.: US 10,786,465 B2
(45) Date of Patent: Sep. 29, 2020

(54) POLYMER/COPOLYMER NANOPARTICLES CONJUGATED TO GAMBOGIC ACID

(71) Applicant: The Texas A&M University System, College Station, TX (US)

(72) Inventors: Naga Venkata Ravi Kumar Majeti, College Station, TX (US); Raghu Ganugula, College Station, TX (US); Meenakshi Arora, College Station, TX (US); Prabhjot Saini, Greenville, SC (US)

(73) Assignee: The Texas A&M University System, College Station, TX (US)

(*) Notice: Subject to any disclaimer, the term of this patent is extended or adjusted under 35 U.S.C. 154(b) by 0 days.

(21) Appl. No.: 15/748,327

(22) PCT Filed: Jul. 27, 2016

(86) PCT No.: PCT/US2016/044304
§ 371 (c)(1),
(2) Date: Jan. 29, 2018

(87) PCT Pub. No.: WO2017/019792
PCT Pub. Date: Feb. 2, 2017

(65) Prior Publication Data
US 2018/0214386 A1    Aug. 2, 2018

Related U.S. Application Data

(60) Provisional application No. 62/197,461, filed on Jul. 27, 2015.

(51) Int. Cl.
*A61K 9/51*    (2006.01)
*B82Y 30/00*    (2011.01)
(Continued)

(52) U.S. Cl.
CPC .......... *A61K 9/5192* (2013.01); *A61K 9/5153* (2013.01); *A61K 47/549* (2017.08);
(Continued)

(58) Field of Classification Search
CPC ................ A61K 9/5192; A61K 47/549; A61K 47/6937; A61K 9/5153; B82Y 5/00; B82Y 30/00
See application file for complete search history.

(56) References Cited

U.S. PATENT DOCUMENTS

2010/0166865 A1   7/2010   Kumar et al.
2010/0290982 A1*   11/2010   Ranjan ................. A61K 9/5153
                                           424/1.11
(Continued)

FOREIGN PATENT DOCUMENTS

WO    WO-2015/081096 A2    6/2015

OTHER PUBLICATIONS

Yao et al, Nanoparticle delivery and combination therapy of gambogic acid and all-trans retinoic acid, Int J Nanomedicine; 9: 3313-3324 (Year: 2014).*

*Primary Examiner* — Carlos A Azpuru
(74) *Attorney, Agent, or Firm* — Winstead PC

(57) ABSTRACT

A composition comprising a nanoparticle, wherein the nanoparticle comprises a polymer/copolymer conjugated to a moiety is disclosed. A method of forming a nanostructure includes stirring poly(lactide-co-glycolide) (PLGA) and 11-Ethyl-3-(dimethylaminopropyl) carbodiimide (EDC) in $CH_2Cl_2$ to create a PLGA mixture, n-boc-ethyelenediamine and N,N-Diisopropylethylamine (DIEA) are added to the PLGA mixture to create a reaction mixture. The reaction mixture is then precipitated in cold diethyl ether to form a purified polymer, which is then dried. The dried and purified polymer is then reconstituted in $CH_2Cl_2$:TFA solution and (Continued)

ILLUSTRATION KEY:

FLUORESCENCE ∿∿
HUMAN TfR
1° ANTIBODY FOR TfR
2° ANTIBODY FOR TfR
7-PEPTIDE ⁀⁀
FLUORESCENT PLGA-GA-NS stirred under inert conditions. The product of the reconstituting step is evaporated to form a clear viscous residue that is dissolved in $CH_2Cl_2$ and then precipitated in cold ether to form a polymer. These functional polymers can encapsulate a variety of bioactives forming nanosystems improving the performance of bioactives.

13 Claims, 2 Drawing Sheets

(51) Int. Cl.
  *A61K 47/69* (2017.01)
  *A61K 47/54* (2017.01)
  *B82Y 5/00* (2011.01)
(52) U.S. Cl.
  CPC .......... *A61K 47/6937* (2017.08); *B82Y 30/00* (2013.01); *B82Y 5/00* (2013.01)

(56) References Cited

U.S. PATENT DOCUMENTS

| | | |
|---|---|---|
| 2011/0104265 A1 | 5/2011 | Mousa et al. |
| 2011/0275686 A1 | 11/2011 | Langer et al. |
| 2014/0005379 A1* | 1/2014 | Gu .................. A61K 47/26 536/112 |

\* cited by examiner

POLYMER/COPOLYMER NANOPARTICLES CONJUGATED TO GAMBOGIC ACID

CROSS-REFERENCE TO RELATED APPLICATIONS

This application claims priority to U.S. Provisional Application Ser. No. 62/197,461 filed on Jul. 27, 2015, which is incorporated herein by reference in its entirety.

BACKGROUND OF THE INVENTION

The development of nanostructures based on polylactide (PLA) or its copolymer poly(lactide-co-glycolide) (PLGA) has proven to be a mode of a delivery via invasive routes, while oral administration remains a challenge as the absorption is quite poor when administered orally due to passive transport mechanisms through the gastrointestinal tract. The claimed invention aims to ameliorate this shortcoming by providing a new platform for the oral delivery of drugs that have not been successful in the past.

Receptor-mediated drug delivery using functional polymer nanosystems (NS) has been explored over the years to enhance the therapeutic index of drugs. The recent use of receptor-mediated uptake in the gastrointestinal tract (GIT) presents an exciting opportunity for targeted and enhanced delivery of NS via vitamin B12, folate-receptor, neonatal fc receptor, asialoglycoprotein receptor, GLUT transporters and transferrin-receptor (TfR). Due to its high expression, TfR is one of the prominent receptors explored for transport of NS across GIT and blood-brain barriers (BBB). TfR, responsible for the transport of iron bound transferrin across the GIT, is expressed in varying intensity across the GIT with the highest density in small intestine in villous cells of the epithelium. Although TfRs are believed to be mainly concentrated on the basal and lateral sides of the epithelial cells in the small intestine, there are reports suggesting their presence on the apical side and concentration in clathrin-coated pits along the free cell margins. The ligands currently in use for receptor-mediated drug delivery must out-compete endogenous ligands in order to bind to the active site facilitating the transport.

SUMMARY OF THE INVENTION

The current methods for targeted drug delivery utilize ligands that must out-compete endogenous ligands in order to bind to the active site facilitating the transport. To address this limitation, a non-competitive active transport strategy is used to overcome intestinal barriers in the form of tunable nanosystems (NS) for transferrin receptor (TfR) utilizing gambogic acid (GA), a xanthanoid, as its ligand. The NS made using GA conjugated poly(lactide-co-glycolide) (PLGA) have shown non-competitive affinity to TfR evaluated in cell/cell-free systems. The fluorescent PLGA-GA NS exhibited significant intestinal transport and altered distribution profile compared to PLGA NS in vivo. The PLGA-GA NS loaded with cyclosporine A (CsA), a model peptide, upon peroral dosing to rodents led to maximum plasma concentration of CsA at 6 hours as opposed to 24 hours with PLGA-NS with at least 2-fold higher levels in brain at 72 hours. The proposed approach offers new prospects for peroral drug delivery and beyond.

The composition of the claimed invention makes use of a copolymer conjugated to a moiety in order to facilitate the absorption of a bioactive and to target a specific site. A copolymer, such as PLA/PLGA, must be conjugated to a moiety, e.g., gambogic acid (GA), galactose (GaL) via a linker. The synthesized conjugate is then able to form stable nanoparticles by emulsion-diffusion-evaporation methods that entrap drugs or drug like compounds. The use of moieties within the composition allows for a higher efficacy and enhanced absorption due to the nanoparticle's surface expression making the particle accessible to the respective receptor on the target site.

A composition comprising a nanoparticle, wherein the nanoparticle comprises a polymer/copolymer conjugated to a moiety is disclosed. A method of forming a nanostructure includes stirring poly(lactide-co-glycolide) (PLGA) and 1-Ethyl-3-(dimethylaminopropyl) carbodiimide (EDC) in $CH_2Cl_2$ to activate the carboxyl group of PLGA. n-boc-ethyelenediamine and N,N-Diisopropylethylamine (DIEA) are added to the PLGA mixture and reaction is continued under inert atmosphere for 18 h. The reaction mixture is then precipitated in cold diethyl ether to form a purified polymer, which is then dried. The dried and purified polymer is then reconstituted in $CH_2Cl_2$:TFA solution to deprotect the ethylenedimaine (EDA) coupled to PLGA. The solvent at the end of the deprotection step is evaporated to get a clear viscous residue that is dissolved in $CH_2Cl_2$ and then precipitated in cold ether to obtain PLGA-EDA polymer.

BRIEF DESCRIPTION OF THE DRAWINGS

For a more complete understanding of the present invention and for further objects and advantages thereof, reference may now be had to the following description taken in conjunction with the accompanying drawings in which.

DESCRIPTION OF EXEMPLARY EMBODIMENTS

Various embodiments of the present invention will now be described more fully with reference to the accompanying drawings. The invention may, however, be embodied in many different forms and should not be construed as limited to the embodiments set forth herein.

Embodiments of the claimed invention are directed to the development of nanostructures based on poly(lactide-co-glycolide) (PLGA) conjugated to ligands that facilitate the absorption of entrapped bioactives through the intestine.

In an embodiment of the invention, gambogic acid (GA) conjugated poly(lactide-co-glycolide) is synthesized by linking GA to the carboxyl end groups of PLGA via an ethylenediamine linker using carbodiimide chemistry. The final product may be confirmed using NMR by the appearance of amide peaks linking the amine ends of ethylenediamine to PLGA and GA. Stable nanoparticles can be formed from the PLGA-GA polymer via simple emulsion techniques with a size profile of about 90-150 mm as revealed by size distribution observed using a dynamic light scattering system. X-ray photoelectron spectroscopy (XPS) analysis of the nanostructures reveals their altered surface chemistry with an increased nitrogen content indicating that the ligands are expressed on the surface of the nanostructures. The surface expression of the conjugated ligands on the nanostructures makes them accessible to the respective receptors on the cells.

In an embodiment, PLGA may be conjugated to gambogic acid so that the nanostructure composition may target a specific cell site non-competitively, transferrin receptor.

In some embodiments, PLGA and its ligand counterpart may have their concentrations adjusted in order to facilitate or tailor the delivery and absorption of a bioactive.

WORKING EXAMPLES

Synthesis and Characterization of GA-Conjugated PLGA

Figure 1:
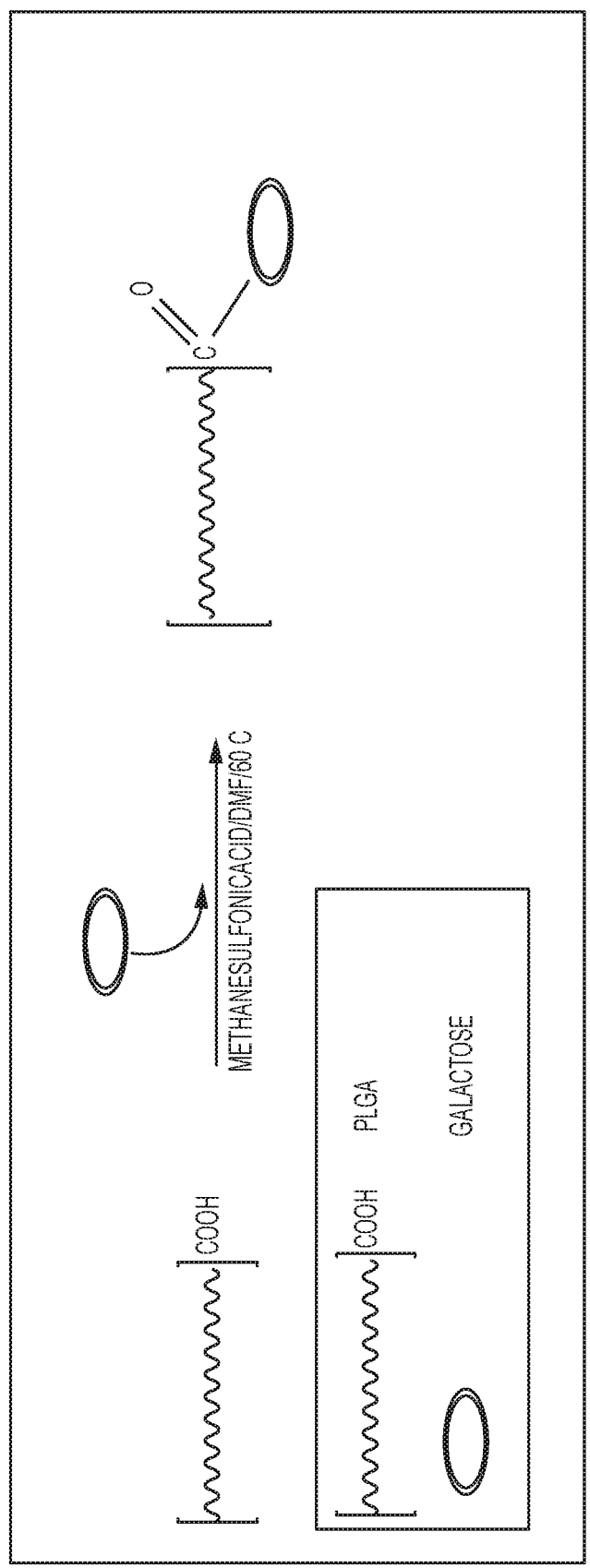
FIG. 1 is an illustration of a reaction scheme of PLGA-GaL.
Figure 2A:
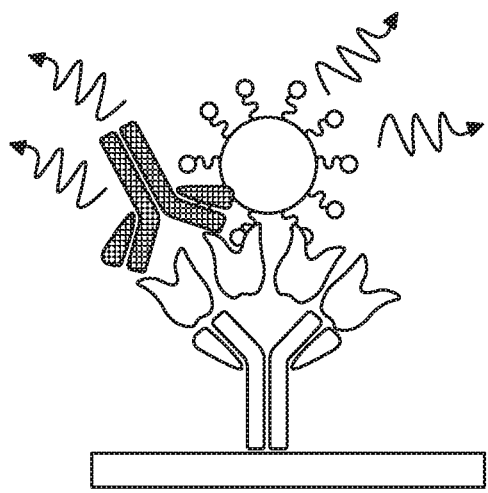
FIG. 2A is an illustration of an ELISA protocol.
Figure 2B:
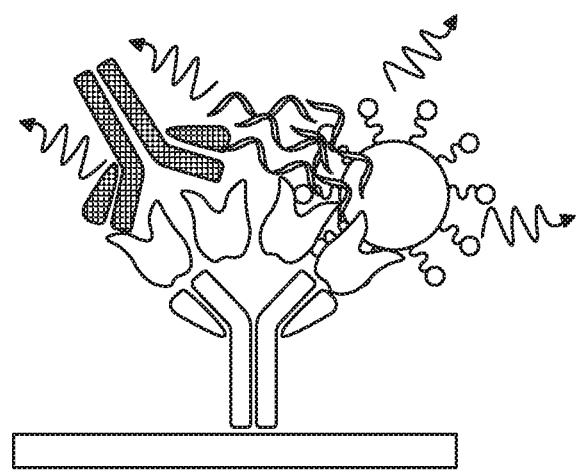
FIG. 2B is an illustration of an ELISA protocol used for a competitive binding assay.

The carboxy-terminal end group of PLGA was activated with 1-ethyl-3-(dimethylaminopropyl) carbodiimide (EDC) and connected to n-boc-ethylenediamine via an amide bond, which was then de-protected to get PLGA-EDA with a free amine group. The amine functionality allowed for the formation of an amide-linkage to the carboxyl group of GA in the subsequent reaction (e.g., see FIG. 2(a)). The covalent bonding of GA to PLGA was confirmed by NMR spectroscopy. The mild reactions employed in the conjugation process yield high amounts of products while preserving the structural integrity of the polymer backbone, as was evident from the GPC and MALDI-MS data, as well as unaltered thermal properties, observed in DSC.

The use of the biocompatible EDA linker to bind GA to PLGA served the dual purpose of activating PLGA end groups and imparting a high level of hydrophilicity to the ligand-terminus of the polymer chains. The hydrophilic end of the polymer chain facilitates the surface expression of ligands on NS during preparation in an aqueous environment. PLGA-GA itself exhibited higher hydrophilicity than PLGA in water contact angle analysis. In addition to PLGA-GA, rhodamine conjugated fluorescent PLGA-Rh was prepared by coupling rhodamine-NHS to PLGA-EDA.

Preparation and Characterization of PLGA-GA NS

To evaluate the avidity of GA activated NS towards TfR, four variations of NS were engineered by blending PLGA-GA and PLGA in varying quantities: PLGA(100%); PLGA-GA(20%)-PLGA(80%); PLGA-GA(60%)-PLGA(40%) and PLGA-GA(100%); (PLGA, PLGA-GA20, PLGA-GA60, and PLGA-GA100). PLGA-GA/PLGA blends in these concentrations yielded didodecyldimethylammonium bromide (DMAB) surfactant exhibited a spherical morphology with a diameter of ~110 nm (PDI ~0.1), which remained unchanged for all four variations of NS. Due to the interaction of the hydrophilic ligand-end of the polymer with the aqueous environment during the emulsification of organic phase carrying PLGA-GA, GA was expressed on the surface of the NS. An increasing trend of the amount of surface nitrogen in NS ranging from 0% to 100% PLGA-GA revealed by the x-ray photon spectra (XPS) indicated the surface expression of EDA, and hence the localization of GA on NS surface. It is ideal for the ligand to be expressed on the surface of the NS to provide access for the cell membrane receptors to bind to the ligands and internalize the NS. UV spectroscopy was also employed for surface characterization of PLGA-GA/PLGA NS following its established use to characterize adsorbed ligands on NS surface.

Incorporation of 4% (w/w) PLGA-Rh in the polymer mixture used to prepare NS yielded fluorescent NS (F-NS), fluorescing at excitation/emission (Ex/Em) wavelengths of 552/575 nm. The F-NS were employed in the cellular uptake, ex vivo intestinal tissue transport and in vivo distribution studies to track the NS.

In addition to non-fluorescent and fluorescent blank NS, cyclosporine A (CsA) loaded PLGA and PLGA-GA100 NS were prepared to evaluate CsA distribution kinetics in rodents. The NS prepared using the methods previously developed had the entrapment efficiency of 45% at 20% (w/w) loading or 90 μg CsA/mg polymer, irrespective of the conjugation status of the polymer. The NS displayed a slightly increased size of 157 nm due to the incorporation of CsA in the polymer matrix. The PLGA-GA and their NS were stable in gastric and intestinal conditions for the transit periods.

For drug entrapment, the pellets of the CsA loaded NS obtained after centrifugation were dissolved in 3 ml acetonitrile. The amount of drug entrapped in the NS was determined by HPLC with a diode array detector (DAD) (Agilent 1220 infinity), using ODS Hypersil (150×4.6 mm; 5 μm) column at 70° C. with acetonitrile: Methanol: 0.05 M Phosphoric acid (45:40:15) as mobile phase eluting at 0.7 ml/min. The wavelength of the DAD was set to 210 nm with 360 nm reference wavelength and a window of ±4 nm. The retention time of CsA was 5.3 minutes. The percent entrapment efficiency of CsA in the NS was calculated using Equation (3).

$$\% EE = \text{Amount of drug loaded} - \text{Amount of drug in supernatant}/\text{Amount of drug loaded} \times 100 \qquad \text{Equation (1)}$$

ELISA Study to Evaluate Non-Competitive Binding of PLGA-GA NS to TfR

GA has been previously shown to have affinity for TfR, independent of transferrin binding. To evaluate the translation of the avidity of GA for TfR in PLGA-GA NS, a sandwich ELISA method was employed. The initial study involved the determination of the effect of surface GA density of NS in their binding affinity to TfR. Fluorescent PLGA, PLGA-GA20, PLGA-GA60 and PLGA-GA100 NS (F-NS) were introduced to 200 ng of TfR (e.g., see FIG. 3*a*). After incubation and washing of the unbound NS, an increase in fluorescence intensity (FI) was seen with the increasing amount of PLGA-GA in the NS, and hence the surface density of GA. An increasing trend was observed in the height and area under the curves in wavelength scans for florescence excitation at 550-600 nm as well as the FI values obtained at 578 nm, λ max for PLGA-Rh. The total H of the NS suspension available in the wells without TfR was also measured in order to ensure that the variation in the FI with TfR was caused by the binding of the NS to the receptor. The initial FI, which was similar for all NS suspensions before the binding assay, was retained only by PLGA-GA100 at the end of the ELISA study, while the FI of others declined with the decrease in the amount of PLGA-GA in the NS. The similar FI for initial unwashed and final bound and washed PLGA-GA100 NS indicated that almost all the NS were bound to TfR. The colorimetric measurements for TfR levels depicted no significant reduction from the initial values signifying that GA does not compete with 2° antibody for TfR.

In the subsequent study, TfR was blocked using 7-peptide, a ligand with high affinity for TfR before treating with PLGA-GA/PLGA F-NS. Due to the lack of information available about the amount of 7-peptide required to completely block TfR, 250 ng of TfR was treated with 25, 75 and 150 ng of 7-peptide followed by estimating TfR levels using 2° TfR antibody. The colorimetric assay suggested no significant difference between the different amounts of 7-peptide used. Based on the results of the aforementioned assay, the highest tested 150 ng dose of 7-peptide was selected to sufficiently block TfR to evaluate the binding of PLGA-GA/PLGA NS to TfR in the presence of 2° antibody (e.g., see FIG. 3(*b*)). Similar to the previous experiment devoid of a second ligand, an increase in FI was observed with the increasing surface GA density from PLGA to PLGA-GA100. The increase in the binding capacity of PLGA-GA NS as a function of the surface density of GA was observed in spite of the decreased free TfR levels due to 7-peptide, confirmed by the colorimetric scans of the subsequently added 2° TfR antibody. Thus, it can be concluded that the ability of GA to bind non-competitively to TfR is preserved in the functionalized PLGA-GA NS.

Transport Studies of PLGA-GA NS with/without Blocking of TfR and Toxicity Evaluation in Cultured Cells Caco-2 (human colon adenocarcinoma cell line) cells are extensively used as in vitro intestinal barrier model as they exhibit differentiated brush border on the apical surface with the expression of intestinal features like microvillus hydrolases, nutrient transporters and receptors including those for transferrin. The cellular uptake of PLGA-GA/PLGA NS followed a pattern similar to their binding affinity to TfR reflected in the ELISA study. It was observed that suspending the NS directly in media or PBS caused excessive agglomeration, thus limiting the uptake by cells. To avoid aggregation, NS (250 µg or 500 µg) were suspended in water (200 µl) and added to the culture wells followed by media after 5 minutes to allow the cells to bind and internalize the freely suspended NS followed by incubation for 1 hour. Fluorescence microscopic investigation of the cell monolayers treated with PLGA-GA/PLGA F-NS revealed an increase in the amount of cellular uptake of the NS with the increase in the surface expression of GA.

This finding was further substantiated by the increase in FI for rhodamine in the monolayers treated with NS with increasing amount of PLGA-GA in the NS. A rightward shift in the cell population plots with respect to control was observed in Fluorescence activated cell sorting/scanning (FACS) corresponding to the increasing amount of rhodamine positive (Rh+) cells. The shift in cell population increased with the increase in the amount of PLGA-GA present in the NS, concurrent with the FI and F-NS distribution observed in the microscopic evaluation. In addition, a separate new intense population of Rh+ cells could be seen in the FACS plots indicative of some cells taking up more NS than others. This intense population of Rh+ cells was more pronounced for the monolayers treated with 500 µg NS. In general, the cellular uptake of NS was higher when treated with larger amount of NS.

To study the non-competitive affinity of PLGA-GA/PLGA NS to TfR in the presence of another ligand, the cells were pre-treated with anti TfR 1° antibody followed by treatment with 500 µg of PLGA-GA/PLGA or PLGA F-NS. TfR blocking did not compromise the cellular uptake of any of the NS variations, confirming the non-competitive binding of GA to TfR. In another experiment, the cells were pre-treated with 10, 20 and 30 µM GA to saturate the GA site on the receptor. In this case, a significant reduction in the uptake of PLGA-GA60 and PLGA-GA100 NS was observed but not for PLGA and PLGA-GA20 NS which rely on the passive uptake mechanisms. These findings substantiate our claim that the PLGA-GA NS employ TfR, non-competitively for their internalization into cells. The PLGA/PLGA-GA NS localization was further confirmed by confocal imagery.

Concentration Dependent Toxicity in Caco-2 Cells

Since GA has been established as a potent anti-cancer agent with cytotoxic capabilities, it was imperative to evaluate the safety of PLGA-GA NS. While no cell death was observed in cells treated with 10 µM molecular GA, significant cell death of 25% and 46% was observed in those treated with 20 and 30 µM GA respectively. The cells treated with 250 µg of all PLGA-GA/PLGA NS and 500 µg of PLGA-100 and PLGA-GA20 did not show any significant cell death compared to control while 11% and 25% cell death was observed in case of cells treated with 500 µg PLGA-GA60 and PLGA-GA100 respectively. Cell death observed in the latter case could be attributed to the cumulative effect of high concentration of polymer and available GA. However, a moderate treatment of 250 µg NS appears to be safe for the cells. The amount of GA present in all the NS in 250 and 500 g was much lower than the established safe dose of 60 mg/kg described in literature.

Ex vivo Transport of PLGA-GA NS through Intestinal Barrier

While caco-2 monolayers provide ample information about the receptor-mediated cellular uptake and safety of PLGA-GA NS, they do not mimic tissue-level transport and binding. To study the transport of the F-NS through the intestinal barriers, an ex vivo intestinal model was employed by using a tubular section of jejunum of Sprague-Dawley (SD) rat, which is one of the intestinal areas with high density of TfR. The sac like structure infused with NS (250 µg/ml) suspended in water was placed in media simulating physiological conditions for 2 hours followed by washing and cryo-sectioning of the tissue for analysis. Concurrent with the observation in caco-2 monolayers, a large influx of NS into the intestinal tissue was observed for PLGA-GA NS with increasing amount surface GA density with highest uptake for PLGA-GA100. The transport of the NS across the intestinal wall was confirmed by their appearance in the surrounding media via DLS and SEM analyses. These findings establish a clear role of active transport mediated by GA, since very low amount of F-NS without GA were absorbed by passive means.

Kinetics of Fluorescent PLGA-GA NS

The in vivo kinetics of PLGA-GA or PLGA F-NS were studied following a 50 mg/kg (~16 mg/rat) peroral dose and evaluation of red blood cells (RBC), plasma, small intestine, liver, spleen, kidneys and brain tissues for rats sacrificed at 2, 12 and 24 hours. A gradual increase in RBC associated PLGA NS levels was observed over 24 hours while PLGA-GA NS showed an initial increase until 12 hours followed by a decline. The RBC associated PLGA-GA NS levels were lower than PLGA NS at all time points. Both NS displayed a similar concentration trend during 24 hours in plasma as RBC, however the concentration of PLGA-GA NS was about 2-fold higher than PLGA NS at 12 hours but slightly lower at 24 hours. This finding suggests that PLGA-GA NS have a preferential residence in plasma over association with RBC during circulation, which can be attributed to the hydrophilic nature of PLGA-GA NS.

The presence of PLGA-GA NS in SI was highest at 2 hours followed by a gradual decrease at 12 hours with almost negligible amount present in the intestinal tissue at 24 hours, indicative of complete transport across the intestinal barrier in the given timeframe. The fast absorption of PLGA-GA NS can be attributed to TfR mediated active transport. In comparison, a considerable amount of PLGA NS remained unabsorbed as indicated by their persistent levels observed in the tissue sections at all time points. A similar trend was observed in spleen where PLGA NS prevailed in high amounts until 24 hours while PLGA-GA NS had a higher splenic concentration only at 2 hours, but very low and decreasing concentrations at 12 and 24 hours, indicating possible recirculation. In contrast, the concentration of PLGA-GA NS was highest in liver at 12 hours with much lower concentrations at 2 and 24 hours. The low levels of PLGA-GA NS in liver and spleen, the major organs of reticuloendothelial system (RES) responsible for clearance of foreign bodies including NS, reflect the recirculation of NS. Research has shown that a majority of NS reside within the RES organs for over 2 weeks after being cleared from circulation. While this effect was evident in the case of PLGA NS for the duration of the study, it was not observed for PLGA-GA NS. The recirculation of PLGA-GA NS was further affirmed by the appreciable levels of these NS in plasma at 24 hours despite negligible concentration in small intestine, eliminating the possibility of transport of any residual unabsorbed NS from SI as in the case of PLGA NS. The hydrophilicity of PLGA-GA NS plays an integral part in their recirculation, as they can evade opsonization and hence accumulation in RES and phagocytosis by macrophages. Renal clearance can also be ruled out for the NS considering their size which is larger than the renal filtration cut-off and their absence in glomerular areas in kidney sections.

TfR has been established as a resident receptor on the brain vasculature involved in the uptake and transport of transferrin and anti-TfR antibodies across the BBB. TfR has been exploited as a potential target to deliver drugs and drug carrier systems across the BBB. In the present study, the PLGA-GA NS were able to penetrate the BBB as is evident by their accumulation in brain tissue in appreciable amount, with maximum concentration at 2 hours followed by a statistically insignificant decline at 12 hours and further decline at 24 hours. In contrast, insignificant amount of PLGA NS was observed at 12 and 24 hours. In comparison to PLGA NS, the concentration of PLGA-GA NS in brain accounted to about 7- and 4-folds at 2 and 12 hours respectively.

Cyclosporine A (CsA) Kinetics

A drug kinetics study for encapsulated CsA was performed in SD rats following a single peroral dose of 15 mg/kg plain or encapsulated CsA in PLGA and PLGA-GA NS. Plasma concentration of CsA between 0-72 hours revealed that a concentration maximum ($C_{max}$) was reached at 12 hours (maximum time taken, $T_{max}$) for plain CsA and 24 hours for PLGA NS, but much sooner at 6 hours for PLGA-GA NS. This finding resonates with the results of the plasma concentration of F-NS with maximum FI at 24 and 12 hours for PLGA and PLGA-GA NS respectively. The plasma concentration profiles, area under the curve ($AUC_{0-72}$) and $C_{max}$ for CsA were the highest for PLGA-GA NS indicative of a larger amount of these NS being transported across the intestinal barrier compared to PLGA NS and plain CsA. The significant decrease in $T_{max}$ for PLGA-GA NS offers renewed hope for the PLGA delivery systems which otherwise are not suitable for drugs needing immediate release profiles or those with a narrow therapeutic index (e.g., CsA) where $C_{max}$ can be detrimental for efficacy while maintaining the AUC. The concentration of CsA in liver at the termination of study (72 hours) was lower for PLGA-GA NS than PLGA NS but higher than plain CsA. On the other hand, brain had a 2-fold higher concentration of CsA in PLGA-GA NS group than PLGA NS, following the trend observed in vivo F-NS distribution study. PLGA and PLGA-GA NS show an opposing trend of CsA concentration in brain compared to plasma where CsA concentration is higher for PLGA NS than PLGA-GA NS. This finding is indicative of enhanced absorption of PLGA-GA NS in tissues without being restricted to RES or plasma. Thus, it can be concluded that the PLGA-GA NS with encapsulated drug can effectively deliver the drug payload across the intestinal barrier and to target organs with high TfR density, like brain.

Example 1—Synthetic Processing of Amination of PLGA Using EDA

PLGA (500 mg; 0.0161 mmol) was stirred with 1-Ethyl-3-(dimethylaminopropyl) carbodiimide (EDC) (15.43 mg; 0.0805 mmol) in 5 ml $CH_2Cl_2$ for 30 minutes. Subsequently, n-boc-ethyelenediamine (12.90 mg; 12.75 µl; 0.0805 mmol) and N,N-Diisopropylethylamine (DIEA) (10.40 mg; 4.02 µl; 0.0805 mmol) were added and the reaction was continued under inert conditions for 18 hours at room temperature. The reaction mixture was precipitated in cold diethyl ether to get a white polymer and further purified by washing with diethyl ether. The purified polymer was dried under vacuum to get 483 mg of dry powder, which was reconstituted in 3.3 ml 10:1 $CH_2Cl_2$:TFA solution and stirred under inert conditions for 1 hour. The solvent was evaporated on a rotary evaporator to get a clear viscous residue which was dissolved in 3 ml $CH_2Cl_2$ and precipitated in cold ether. The polymer thus obtained was dried under vacuum to a constant dry weight (431 mg).

Example 2—Conjugation of Gambogic Acid to Aminated PLGA of Example 1

GA (25.84 mg; 0.0411 mmol) and EDC (9.46 mg; 0.043 mmol) were first dissolved in $CH_2Cl_2$ (1 ml) and stirred under inert conditions for 30 minutes. To the bright orange solution thus obtained, a solution of PLGA-EDA (424 mg; 0.0137 mmol) and DIEA (6.37 mg; 8.6 µl; 0.0493 mmol) in $CH_2Cl_2$ (2 ml) was added. The reaction mixture was further stirred for 18 hours and then precipitated in 50 ml cold diethyl ether. The polymer was purified by dissolving in 3 ml $CH_2Cl_2$ and precipitating in cold diethyl ether. Finally, the polymer was washed with distilled water and dried under vacuum to a constant dry weight (376 mg).

Example 3—Conjugation of Lactobionic Acid (LBA) to Aminated PLGA of Example 1

LBA (26.01 mg; 0.0726 mmol) and EDC (15.32 mg; 0.0799 mmol) were first dissolved in DMF (2 ml) and stirred under inert conditions for 30 minutes. A solution of PLGA-EDA (750 mg; 0.0242 mmol) and DIEA (10.33 mg; 13.92 µl; 0.0799 mmol) in DMF (3 ml) was subsequently added to the reaction vessel and the reaction was continued at room temperature and under inert atmosphere for 18 hours. The product was recovered by precipitation and repeated washing in cold water and dried under vacuum to a constant dry weight (554.5 mg).

Example 4—Conjugation of Galactose to PLGA

PLGA (1.0 g; 0.0323 mmol) and galactose (58.19 mg; 0.323 mmol) dissolved in DMF (5 ml) and stirred at 60° C. under inert atmosphere for 24 hours in the presence of methane sulfonic acid (31.04 mg; 20.96 µl; 0.323 mmol). The reaction mixture was then cooled to room temperature and the product was recovered by precipitation and repeated washings with cold water. The PLGA-GaL thus obtained was then dried to a constant weight under vacuum (926 mg).

Example 5—Conjugation of Arginylglycylaspartic Acid (RGD Peptide) to PLGA

PLGA (150 mg; 0.0048 mmol) and EDC (4.64 mg; 0.0242 mmol) were stirred in DMF (2 ml) for 30 minutes at room temperature, under inert atmosphere. RGD (8.33 mg; 0.0242 mmol) pre-dissolved in DMF (1 ml) and DIEA (3.13 mg; 4.22 µl; 0.0242 mmol) were subsequently added to the reaction vessel and the reaction was continued at room temperature and under inert atmosphere for 18 hours. The product was recovered by precipitation in water, further purified by washing again with water and dried under vacuum to a constant dry weight (69 mg).

Example 6—Conjugation of Fluorescent Probe, Fluorescein to Aminated PLGA of Example 1

NHS-Fluorescein (4.5 mg; 0.0095 mmol), PLGA-EDA (35 mg; 0.0019 mmol) and DIEA (1.23 mg, 1.65 µl; 0.0095 mmol) were dissolved in DMF (1 ml) and stirred in an amber vessel under inert conditions for 18 hours. The reaction mixture was then poured into 50 ml distilled water to precipitate the polymer. The polymer was further washed with distilled water twice to remove residual unreacted NHS-Rhodamine and dried under vacuum to a constant dry weight.

Example 7—Conjugation of Fluorescent Probe Rhodamine to Aminated PLGA of Example 1

NHS-Rhodamine (1.7 mg; 0.0032 mmol), PLGA-EDA (50 mg; 0.0016 mmol) and DIEA (0.414 mg, 0.56 µl; 0.0032 mmol) were dissolved in DMF (1 ml) and stirred in an amber vessel under inert conditions for 18 hours. The reaction mixture was then poured into 15 ml distilled water to precipitate the polymer. The polymer was further washed with distilled water twice to remove residual unreacted NHS-Rhodamine and dried under vacuum to a constant dry weight (39 mg).

Example 8—Conjugation of l-Lysine to PLGA

PLGA (150 mg; 0.0048 mmol) and EDC (4.64 mg; 0.0242 mmol) were stirred in DMF (2 ml) for 30 minutes at room temperature, under inert atmosphere. L-Lysine (3.54 mg; 0.0242 mmol) pre-dissolved in DMF (1 ml) and DIEA (3.13 mg; 4.22 µl; 0.0242 mmol) were subsequently added to the reaction vessel and the reaction was continued at room temperature and under inert atmosphere for 18 hours. The product was recovered by precipitation in water, further purified by washing again with water, and dried under vacuum to a constant dry weight.

Example 9—Conjugation of Cysteine to PLGA

PLGA (150 mg; 0.0048 mmol) and EDC (4.64 mg; 0.0242 mmol) were stirred in DMF (2 ml) for 30 minutes at room temperature, under inert atmosphere. L-Lysine (2.93 mg; 0.0242 mmol) pre-dissolved in DMF (1 ml) and DIEA (3.13 mg; 4.22 µl; 0.0242 mmol) were subsequently added to the reaction vessel and the reaction was continued at room temperature and under inert atmosphere for 18 hours. The product was recovered by precipitation in water, further purified by washing again with water, and dried under vacuum to a constant dry weight.

Example 10—Conjugation of Arginine to PLGA

PLGA (150 mg; 0.0048 mmol) and EDC (4.64 mg; 0.0242 mmol) were stirred in DMF (2 ml) for 30 minutes at room temperature, under inert atmosphere. Arginine (4.22 mg; 0.0242 mmol) pre-dissolved in DMF (1 ml) and DIEA (3.13 mg; 4.22 µl; 0.0242 mmol) was subsequently added to the reaction vessel and the reaction was continued at room temperature and under inert atmosphere for 18 hours. The product was recovered by precipitation in water, further purified by washing again with water, and dried under vacuum to a constant dry weight.

Example 11—Conjugation of Hesperetin to PLGA

PLGA (150 mg; 0.0048 mmol) and EDC (4.64 mg; 0.0242 mmol) were stirred in DMF (1 ml) at room temperature and inert atmosphere for 30 minutes. Hesperetin (7.31 mg; 0.0242 mmol) and DMAP (0.296 mg; 0.00242 mmol) pre-dissolved in 1 ml DMF were subsequently added to the stirring solution and the reaction was continued at these conditions for 18 hours. The product was obtained by precipitation in cold water. The polymer was further washed twice and dried under vacuum to a constant dry weight.

Example 12—Conjugation of Naringenin to PLGA

PLGA (150 mg; 0.0048 mmol) and EDC (4.64 mg; 0.0242 mmol) were stirred in DMF (1 ml) at room temperature and inert atmosphere for 30 minutes. Hesperetin (6.59 mg; 0.0242 mmol) and DMAP (0.296 mg; 0.00242 mmol) pre-dissolved in 1 ml DMF were subsequently added to the stirring solution and the reaction was continued at these conditions for 18 hours. The product was obtained by precipitation in cold water. The polymer was further washed twice and dried under vacuum to a constant dry weight.

Example 13—Conjugation of Paclitaxel to PLGA

PLGA (150 mg; 0.0048 mmol) and EDC (4.64 mg; 0.0242 mmol) were stirred in DMF (1 ml) at room temperature and inert atmosphere for 30 minutes. Paclitaxel (20.66 mg; 0.0242 mmol) and DMAP (0.296 mg; 0.00242 mmol) pre-dissolved in 0.5 ml DMF were subsequently added to the stirring solution and the reaction was continued at these conditions for 18 hours. The product was obtained by precipitation in cold 1:1 mixture of ethanol and ethyl ether. The polymer was further washed twice and dried under vacuum to a constant dry weight.

Example 14—Conjugation of Cisplatin to PLGA

PLGA (150 mg; 0.0048 mmol) and EDC (4.64 mg; 0.0242 mmol) were stirred in DMF (1 ml) at ambient temperature and under inert atmosphere for 30 minutes. Cisplatin (7.26 mg; 0.0242 mmol) predissolved in DMF (1 ml) and DIEA (3.13 mg; 4.22 µl; 0.0242 mmol) were subsequently added to the reaction flask and the reaction was carried out in the dark under inert atmosphere and room temperature for 24 hours. The conjugated polymer was recovered by precipitation in water. The polymer was further washed twice with water and dried under vacuum to a constant dry weight.

Example 15—Conjugation of Gemcitabine to PLGA

PLGA (150 mg; 0.0048 mmol) and EDC (4.64 mg; 0.0242 mmol) were stirred in DMF (1 ml) at room temperature and inert atmosphere for 30 minutes. Gemcitabine (6.4 mg; 0.0242 mmol) predissolved in DMF (1 ml) and DIEA (3.13 mg; 4.22 µl; 0.0242 mmol) were subsequently added to the reaction flask and the reaction was continued for 24 hours. A yellow conjugated polymer was obtained by precipitation in water. The polymer was further washed twice with water and dried under vacuum to a constant dry weight.

Example 16—Conjugation of Withaferin A to PLGA

PLGA (100 mg; 0.0032 mmol) and EDC (3.07 mg; 0.016 mmol) were stirred in DMF (1 ml) at room temperature and inert atmosphere for 30 minutes. Withaferin A (7.53 mg; 0.016 mmol) and DMAP (0.194 mg; 0.0016 mmol) pre-dissolved in 0.5 ml DMF were subsequently added to the stirring solution and the reaction was continued at these conditions for 18 hours. The product was obtained by precipitation in cold water. The polymer was further washed twice and dried under vacuum to a constant dry weight.

Example 17—Conjugation of Diagnostic Agents to PLGA

PLGA can be functionalized with diagnostic agents e.g. MRI and ultrasound contrast agents, Near-IR fluorescent agents etc. by coupling them to the carboxyl or amine functionality of aminated PLGA via ester or amide bonds based on the available functional unit of the agent. Both the processes involve activation of carboxyl on either the polymer or the diagnostic moiety by EDC followed by either amination in the presence of DIEA or esterification in the presence of DMAP. Alternatively, Fischer esterification can be employed to directly conjugate a moiety with hydroxyl functionality to the carboxyl terminus of PLGA, if the said moiety can withstand higher temperatures and strong acid catalyst.

Example 18—General Description of Nanosystems Preparation

A composition comprising one or more functional polymers (working examples 1-17) can be mixed together to encapsulate drugs forming nanosystems with variable surface characteristics that can alter bio-distribution of drugs.

Conditional language used herein such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it will be understood that various omissions, substitutions, and changes in the form and details of the devices illustrated can be made without departing from the spirit of the disclosure. As will be recognized, the processes described herein can be embodied within a form that does not provide all of the features and benefits set forth herein, as some features can be used or practiced separately from others. The scope of protection is defined by the appended claims rather than by the foregoing description. All changes which come within the meaning and range of equivalency of the claims are to be embraced within their scope.

The invention claimed is:

1. A composition comprising a nanoparticle, wherein the nanoparticle comprises a polymer/copolymer conjugated to gambogic acid.

2. The composition of claim 1, wherein a concentration of the polymer/copolymer may be adjusted to suit a specific target.

3. The composition of claim 1, wherein the composition possesses target specificity.

4. The composition of claim 1, wherein the polymer/copolymer are polylactide, poly(lactide-co-glycolide) or polycaprolactone.

5. The composition of claim 1, wherein the composition facilitates absorption of a desired bioactive.

6. The composition of claim 1, wherein surface expression of the nanoparticle makes the polymer/copolymer conjugated to gambogic acid accessible to respective receptors on a target site.

7. The composition of claim 1, wherein the composition expresses covalently bound ligands to interact non-competitively with receptors on cell membranes for receptor-mediated uptake.

8. The composition of claim 1, wherein the composition comprises a ligand with amine, carboxyl or hydroxyl functionality.

9. The composition of claim 1, wherein the a conjugated polymer/copolymer can form stable nanoparticles via emulsion-diffusion techniques.

10. The composition of claim 1, wherein the gambogic acid is linked to carboxyl end groups of the polymer/copolymer via a linker.

11. The composition of claim 10, wherein the linker is an ethylenediamine linker.

12. The composition of claim 1, wherein the composition includes more than one ligand to tailor a distribution profile of the composition in a subject based on needs of a disease and/or drugs encapsulated.

13. A method of producing the composition of claim 1, the method comprising:
    synthesizing a copolymer conjugated with gambogic acid; and
    preparing the nanoparticles by utilizing an emulsion-diffusion-evaporation method to entrap a desired bioactive within the nanoparticles.

* * * * *